US008198032B2

(12) United States Patent  
Zabe et al.

(10) Patent No.: US 8,198,032 B2
(45) Date of Patent: Jun. 12, 2012

(54) MULTI-ANALYTE AFFINITY COLUMN

(75) Inventors: Nancy A. Zabe, Waltham, MA (US); Christopher J. Basker, Worcester, MA (US)

(73) Assignee: Waters Technologies Corporation, Milford, MA (US)

( * ) Notice: Subject to any disclaimer, the term of this patent is extended or adjusted under 35 U.S.C. 154(b) by 913 days.

(21) Appl. No.: 12/065,466

(22) PCT Filed: Nov. 17, 2006

(86) PCT No.: PCT/US2006/044739
§ 371 (c)(1), (2), (4) Date: Sep. 12, 2008

(87) PCT Pub. No.: WO2007/059316
PCT Pub. Date: May 24, 2007

(65) Prior Publication Data
US 2009/0035786 A1    Feb. 5, 2009

Related U.S. Application Data

(60) Provisional application No. 60/738,330, filed on Nov. 17, 2005.

(30) Foreign Application Priority Data

Dec. 21, 2005  (EP) ..................... 50281021

(51) Int. Cl.
*G01N 33/538* (2006.01)

(52) U.S. Cl. ......................... 435/7.1; 435/7.4

(58) Field of Classification Search .................. None
See application file for complete search history.

(56) References Cited

U.S. PATENT DOCUMENTS

| | | | |
|---|---|---|---|
| 4,818,687 | A | 4/1989 | Groopman et al. |
| 4,859,611 | A | 8/1989 | Groopman et al. |
| 5,178,832 | A | 1/1993 | Phillips et al. |
| 5,707,818 | A | 1/1998 | Chudzik et al. |
| 6,498,010 | B1 | 12/2002 | Fitzgerald et al. |
| 2005/0100959 | A1 | 5/2005 | Sinbanda et al. |
| 2007/0048787 | A1 | 3/2007 | Zabe et al. |
| 2007/0117218 | A1 | 5/2007 | Zabe et al. |
| 2007/0117219 | A1 | 5/2007 | Zabe et al. |

FOREIGN PATENT DOCUMENTS

| | | |
|---|---|---|
| CA | 2529159 A1 | 4/2006 |
| CA | 2629472 A1 | 5/2007 |
| EP | 1757349 | 2/2007 |
| EP | 1787698 | 5/2007 |
| EP | 1787698 A1 | 5/2007 |
| EP | 1787700 A1 | 5/2007 |
| EP | 1957629 A0 | 8/2008 |
| WO | WO2007/059316 A2 | 5/2007 |

OTHER PUBLICATIONS

Visconti et al. (J. Chromatography A., 1075:151-158, 2005).*
Archived Pickering Laboratories Homepage (2003) (1 page) http://web.archive.org/web/20040802070622/http://pickeringlabs.com/ (Aug. 2, 2004 archived Pickering Laboratories website).
Archived Pickering Laboratories "Online Catalog: Table of Contents" (2003) (1 page) http://web.archive.org/web/20040812110937/www.pickeringlabs.com/catalog/ (Aug. 2, 2004 archived Pickering Laboratories website).
Archived Ofitserova et al., "Multi-Residue Mycotoxin Analysis: Single Run Analysis of Deoxynivalenol, Aflatoxins, OchratoxinA, Zearalenone and Fumonisin by HPLC and Post-column Derivatization" Method Abstract for Post-column Liquid Chromatography 203 (2003) (2 pages) http://web.archive.org/web/20040806010721/pickeringlabs.com/catalog/M_203.php4 (Aug. 2, 2004 archived Pickering Laboratories website).
Archived Ofitserova et al., "Multi-Residue Mycotoxin Analysis: Single Run Analysis of Deoxynivalenol, Aflatoxins, OchratoxinA, Zearalenone and Fumonisin by HPLC and Post-column Derivatization" Method Abstract for Post-column Liquid Chromatography 203 (2004) (2 pages) (Aug. 2, 2004 archived Pickering Laboratories website) (pdf link from Item CC above).
Archived "Multi-Residue Mycotoxin Analysis Column" (2003) (2 pages)  http://web.archive.org/web/20040807201548/www.pickeringlabs.com/catalog/CCG_MRM . . . (Aug. 2, 2004 archived Pickering Laboratories website).
Archived "Other Post-column Analysis Kits" (2003) (2 pages) http://web.archive.org/web/20040807195948/www.pickeringlabs.com/catalog/AK_OPCA . . . (Aug. 2, 2004 archived Pickerin Laboratories website).
Archived Pickering Laboratories HPLC Post-column Derivatization 2003 Product Catalog (cover—1 page) (Aug. 2, 2004 archived Pickering Laboratories website) (pdf link from Item CB above).
"About Pickering Laboratories," Archived Pickering Laboratories HPLC Post-column Derivatization 2003 Product Catalog (p. 1) (Aug. 2, 2004 archived Pickering Laboratories website) (pdf link from Item CB above).
"Table of Contents," Archived Pickering Laboratories 2003 Product Catalog (1 page) (Aug. 2, 2004 archived Pickering Laboratories website) (pdf link from Item CB above).

(Continued)

*Primary Examiner* — Nita M Minnifield
*Assistant Examiner* — Brian J Gangle
(74) *Attorney, Agent, or Firm* — Edwards Wildman Palmer LLP; Peter C. Lauro, Esq.; Kathryn A. Piffat, Esq.

(57) ABSTRACT

A multi-analyte column is disclosed. The column may contain at least one unit of resin having ochratoxin specific affinity and, for each unit of resin having ochratoxin specific affinity, the column further contains about 0.95 to 1.05 units of resin containing antibody having specificity for zearalenone, about 1.9 to 2.1 units of resin containing antibody having specificity for aflatoxin, about 2.35 to 2.65 units of resin containing antibody having specificity for fumonisin, about 2.8 to 3.2 units of resin containing antibody having specificity for T-2 (and/or HT-2) and about 4.7 to 5.3 units of resin containing antibody having specificity for deoxynivalenol. One unit of resin is the quantity of resin containing antibody that will bind 50 ng of aflatoxin, 500 ng of deoxynivalenol, 3300 ng of fumonisin, 50 ng of ochratoxin, 830 ng T-2 (and/or HT-2) or 1140 ng of zearalenone, respectively.

19 Claims, No Drawings

OTHER PUBLICATIONS

"Multi-Residue Mycotoxin Analysis Column," Archived Pickering Laboratories HPLC Post-column Derivatization 2003 Product Catalog (pp. 32-33) (Aug. 2, 2004 archived Pickering Laboratories website) (pdf link from Item CB above).

"Other Post-column Analysis Kits Continued," Archived Pickering Laboratories HPLC Post-column Derivatization 2003 Product Catalog (p. 52) (Aug. 2, 2004 archived Pickering Laboratories website) (pdf link from Item CB above).

Ofitserova et al., "Multi-Residue Mycotoxin Analysis: One Run Analysis of Deoxynivalenol, Aflatoxins, Ochratoxin A, Zearalenone and Fumonisin by HPLC and Post-column Derivatization," Product Abstract for Post-column Liquid Chromatography 203, Archived Pickering Laboratories HPLC Post-column Derivatization 2003 Product Catalog (pp. 68-69) (Aug. 2, 2004 archived Pickering Laboratories website) (pdf link from Item CB above).

"PCX Control: Introducing PC Software for the Pickering Laboratories PCX5200 Post-column Derivatization Instrument," Product Abstract for Post-Column Liquid Chromatography 204, Archived Pickering Laboratories HPLC Post-column Derivatization 2003 Product Catalog (p. 72) (Aug. 2, 2004 archived Pickering Laboratories website) (pdf link from Item CB above).

Archived Pickering Laboratories HPLC Post-column Derivatization 2003 Product Catalog (complete 77 pages: cover & pp. 1-76) (Aug. 2, 2004 archived Pickering Laboratories website) (pdf link from Item CB above).

Benvenuti et al., Waters Poster Reprint No. 720000605EN: "A Novel Approach for Mixed Mycotoxin Analysis," Waters Corporation (Milford, MA: May 2003) (4 pages).

Benvenuti et al., Waters Poster Reprint No. 720000908EN: "A Unified Method for Mixed Mycotoxin Analysis Using UV and Fluorescence Detection," Waters Corporation (Milford, MA: 2004 (1 page).

Benvenuti et al., "Multi-Analyte Mycotoxin Analysis Using UV/Fluorescence with Photochemical Derivatization," 2004 Pittsburg Conference (Pittcon 2004); Chicago, IL; Mar. 7-12, 2004 (4200-2100P).

Krol et al., "Multi-Analyte Mycotoxin Analysis Using LC/MS/MS," 2004 Pittsburg Conference (Pittcon 2004); Chicago, IL; Mar. 7-12, 2004 (6000-700).

Siantar et al., "Immunoaffinity SPE Method Optimization by HPLC: The Influence of Tube Material and Sample Matrix on Mycotoxin Recovery," 2005 Pittsburg Conference (Pittcon 2005); Orlando, FL; Feb. 27-Mar. 4, 2005 (2090-3).

Siantar et al., "The Simultaneous Analysis of Aflatoxins, Deoxynivalenol, Fumonisins, Ochratoxin A and Zearalenone Using Mixed-Bed Immunoaffinity Column Clean-Up and HPLC With Post-Column Derivatization" (ch. 14); in: *Mycotoxin Contamination and Control*; Njapau et. al. (eds); AuthorHosue (Bloomington, IN: 2008), 217-229 (Proceedings of the International Workshop on Mycotoxins, held at the U.S. Food & Drug Administration, College Park, MD on Jul. 22-26, 2002).

Form PCT/ISA/220, WO Oct. 3, 2007, International Search Report.
Form PCT/ISA/237, WO Oct. 3, 2007, Written Opinion of the Interntl Searching Auth.

U.S. Office Action dated Sep. 14, 2010 for U.S. Appl. No. 11/283,159.

Response to Office Communication as filed on Mar. 14, 2011 for U.S. Appl. No. 11/283,159.

Declaration of Dr. Stephen P. Powers dated Mar. 14, 2011 for U.S. Appl. No. 11/283,159.

Siantar et al., "LC/Ultraviolet/Fluorescence and LC/MS/MS Analyses of Multiple Mycotoxins in Spiked Beer Using Immunoaffinity Column Clean-Up;" 2009 American Chemical Society in: Appell et al., Mycotoxin Prevention and Control in Agriculture (ch. 17), ACS Symposium Series (American Chemical Socy.: Washington, D.C. 2010), pp. 247-263.

Precise Numerical Results, MYCO6$_{IN}$1—LC/MS/MS, Mycotoxin Testing System, 2008 VICAM (2 pages) (available at http://vicam.com/multi-analyte-test-kits/myco6in1).

Precise Numerical Results, T-2/HT-2™HPLC, Mycotoxin Testing System, 2009 Waters Corporation (availabe at http://vicam.com/t2-test-kits/t2-ht2-hpic) (2 pages).

Precise Numerical Results, T-2test™HPLC, Mycotoxin Testing System, 2010 Waters Corporation (2 pages) (available at http://vicam.com/t2-test-kits/t2-test-hplc).

VICAM—Cultivating Success through Science, T-2test™HPLC, Instruction Manual #GN-MC9538-1, Mar. 28, 2003 (Vicam, L.P.).

Busby et al. "Food-Borne Mycotoxins and Alimentary Mycotoxicoses", Food Borne Infections and Intoxications. 2$^{nd}$ Ed. 519-610 (1979).

Chan, D. et al., "Simultaneous determination of aflatoxins and ochratoxin a in food using a fully automated immunoaffinity column clean-up and liquid chromatography-fluroscence detection," Journal of Chromatography A, 1059(2004) pp. 13-16.

Chang et al. "Rapid Determination of Deoxynivaienol (Vomitoxin) by Liquid Chromatography Using Modified Romer col. Cleanup". J. Assoc. Off. Anal. Chem. 67(1) 52-54 (1984).

Chang et al. "Rapid High Pressure Liquid Chromatographic Determination of Aflatoxin $M_1$ in Milk and Nonfat Dry Milk". J. Assoc. Off. Anal. Chem. 66(4) 913-917 (1983).

Chang et al. "Short Liquid Chromatographic Method for Determination of Zearalenone and alpha-Zearalenol". J. Assoc. Off. Anal. Chem. 67(4) 741-744 (1984).

Chu. "Immunoassays for Analysis of Mycotoxins". Journal of Food Protection. 47(7) 562-569 (1984).

Dragacci et al. "Immunoaffinity Column Cleanup with Liquid Chromatography for Determination of Aflatoxin $M_1$ in Liquid Milk: Collaborative Study". Journal of AOAC International. 84(2) 437-443 (2001).

Essigman et al. "Structural Identification of the Major DNA Adduct Formed by Aflatoxin $B_1$ in vitro". Journal of Proc. Natl. Acad. Sci. 74(5) 1870-1874 (1977).

Gauch et al. "Rapid and Simple Determination of Aflatoxin $M_1$ in Milk in the Low Parts Per $10^{12}$ Range". Journal of Chromatography. 178 (1979) 543-549.

Gobel and Lusky, "Simultaneous Determination of Aflatoxins, Ochratoxin A, and Zearlenone in Grains by New Immunoaffinity Column/Liquid Chromatograpy," Journal of AOAC International vol. 87, No. 2, 2004, pp. 411-416.

Groopman et al. Quantitation of Aflatoxin $B_1$-modified DNA Using Monoclonal Antibodies. Cancer Research 42 3120-3124 (1982).

Grosso et al. Joint IDF-IUPAC-IAEA (FAO) "Intlerlaboratory Validation for Determining Aflatoxin $M_1$ in Milk by Using Immunoaffinity Clean-Up Before Thin-Layer Chromatography". Food Additives and Contaminants, 21(4) 348-357 (2004).

Hansen, "Affinity Column Cleanup and Direct Fluorescence Measurement of Aflatoxin $M_1$ in Raw Milk". Journal of Food Protection 53(1) 75-77 (1990).

Haugen at al, "Monoclonal Antibody to Aflatoxin $B_1$-Modified DNA Detected by Enzyme Immunoassay". Proc. Natl. Acad. Sci. USA 78 (7) 4124-4127 (1981).

Hertzog et al. "Production of Monoclonal Antibodies to Guanine Imidazole Ring-Opened Aflatoxin $B_1$ DNA, the Persistent DNA Adduct in vivo", Carcinogenesis 3(7) 825-828 (1982).

Hu et al. "Elisa of Picogram Quantities of Aflatoxin $M_1$ in Urine and Milk". Journal of Food Protection 47 (2) 126-127 (1984).

Database Biosis[Online] Isohata E. et al., "Simultaneous Analysis of Several Mycotoxins in Grains by High-Performance Liquid Chromatography Studies on Chemical Analysis of Mycotoxins Part XXII, " Database accession No. PREV199294102752, 1992.

Database Medline [Online] Isohata E. at al., "Studies on chemical analysis of mycotoxin (XXI). A rapid analytical method for aflatoxins by immunoaffinity column chromatography and high performance liquid chromatography," Database accession no. NLM1364335, 1990.

Johnson et al. Development of a Radioimmunoassay Procedure for 4-Acetamidobiphenyl, a Metabolite of the Chemical Carcinogen 4-Aminobiphenyl, in Urine. Journal of Analytical Toxicology 4 86-90 (1980).

Lin et al. "2,3-Dihydro-2-(guan-7yl)-3-hydroxy-aflatoxin $B_1$ , a Major Acid Hydrolysis Product of Aflatoxin $B_1$-DNA or Ribosomal RNA Adducts Formed in Hepatic Microsome-mediated Reactions and in Rat Liver in vivo[1] ". Cancer Research 37, 4430-4438 1977.

Martin et al. "Aflatoxin B-Oxide Generated by Chemical or Enzymic Oxidation of Aflatoxin $B_1$ Causes Guanine Substitution in Nucleic Acids". Nature 267, 863-865 (1977).

Ofitserova et al. "Single Run Analysis of Deoxynivalenol, Aflatoxins, Ochratoxin A, Zearalenone and Fumonisin by HPLC and Post-column Derivatization", XP002377222 URL:http//www.pickeringlabs.com.cn/support/appnotes/MA203.pdf, 2004.

Purchase "Acute Toxicity of Aflatoxins $M_1$ and $M_2$ in One-day-old Ducklings". Fd. Cosmet. Toxicol. 5, 339-342 (1967).

Scott et al., "Application of Immunoaffinity Columns to Mycotoxin Analysis," Journal of AOAC International, vol. 80, No. 5, 1997, pp. 941-949.

Sizaret et al. "Detection of Aflatoxins and Related Metabolites by Radioimmunoassay[1,2,3]" JNCI 69(6) 1375-1381 (1982).

Stubblefield et al. "Reverse Phase Analytical and Preparative High Pressure Liquid Chromatography of Aflatoxins", Journal of the AOAC 60 (4) 784-790 (1977).

Stubblefield et al. "Rapid Liquid Chromatographic Determination of Aflatoxins $M_1$ and $M_2$ in Artificially Contaminated Fluid Milks: Collaborative Study", J. Assoc. Off. Anal. Chem. 69(5) 880-885 (1986).

Stubblefield, "The Rapid Determination of Aflatoxin $M_1$ in Dairy Products". Journal of the American Oil Chemists' Society. 56, 800-802 (1979).

Takeda, "Determination of Aflatoxin $M_1$ in Milk by Reversed-Phase High-Performance Liquld Chromatography", Journal of Chromatography 288, 484-488 (1984).

Trucksess, et al. "Immunoaffinity Column Coupled with Solution Fluorometry or Liquid Chromatography Postcolumn Derivatization for Determination of Aflatoxins in Corn, Peanuts, and Peanut Butter: Collaborative Study". J. Assoc. Off. Anal. Chem 74 (1) 81-88 (1991).

Van Der Gaag et al. "Biosensors and Multiple Mycotoxin Analysis". Food Control 14, 251-254 (2003).

Van Egmond, et al. Improved Method for Confirmation of Identity of Aflatoxins $B_1$ and $M_1$ in Dairy Products and Animal Tissue Extracts. J. Assoc. Off. Anal. Chem. 64(1) 152-155 (1981).

Wogan, Aflatoxin carcinogenesis. IN: Methods in Cancer Research, vol. VII, H. Busch, ed., Academic Press, NY 309-344 (1973).

\* cited by examiner

MULTI-ANALYTE AFFINITY COLUMN

CROSS-REFERENCES TO RELATED APPLICATIONS

The present application is the U.S. National Phase Application, pursuant to 35 U.S.C. §371, of PCT international application Serial No. PCT/US2006/044739, filed Nov. 17, 2006, designating the United States and published in English on May 24, 2007 as publication WO 2007/059316, which claims priority to U.S. Provisional Application Ser. No. 60/738,330, filed Nov. 17, 2005, and to European Application No. 5028102.1, filed Dec. 21, 2005. The entire disclosures of each of the aforementioned patent applications are incorporated herein by this reference.

FIELD OF THE INVENTION

The invention is concerned with affinity columns used for immunological screening for environmentally occurring toxins, for example, those found in food products, and is particularly directed to multi-analyte columns for detecting a plurality of toxins that may be present in a single sample.

BACKGROUND OF THE INVENTION

Awareness of the incidence and effect of human and animal exposure to toxic substances by humans and other animals via food, water, and air is of critical importance to our survival. The detection of toxins such as aflatoxin, ochratoxin, zearalenone, deoxynivalenol, fumonisin and T-2 has become especially important. In particular, screening procedures for assessing the exposure of humans to such toxins may require the ability to quantify both the toxin and its metabolites.

Aflatoxins are a typical example of the compounds for which screening is desired. Aflatoxins are secondary fungal metabolites, mycotoxins, which are produced by *Aspergillus flavus* and *Aspergillus parasiticus* and are structurally a group of substituted coumarins containing a fused dihydrofurofuran moiety. Aflatoxins occur naturally in peanuts, peanut meal, cottonseed meal, corn, dried chili peppers, and the like. However, the growth of the mold itself does not predict the presence or levels of the toxin because the yield of aflatoxin depends on growth conditions as well as the genetic requirements of the species. A variety of aflatoxins, that is types $B_1$, $B_2$, $G_1$, $G_2$, $M_1$ and $M_2$, have been isolated and characterized. Aflatoxin $B_1$ ("$AFB_1$") is the most biologically potent of these aflatoxins and has been shown to be toxic, mutagenic and carcinogenic in many animal species. This mycotoxin is a frequent contaminant of the human food supply in many areas of the world and is statistically associated with increased incidence of human liver cancer in Asia and Africa, in particular (Busby et al., in *Food-Born Infections and Intoxications* (Riemann and Bryan, Editors) Second Edition, Academic Press, Inc., 1979, pp. 519-610; Wogan, G. N. *Methods Cancer Res.* 7:309-344 (1973)).

$AFB_1$ also forms covalently linked adducts with guanine in DNA after oxidative metabolism to a highly reactive 2,3-exo-epoxide, the major adduct product being 2,3-dihydro-2-($N_7$-guanyl)-3-hydroxy-aflatoxin $B_1$ ("$AFB_1$-N7-Gua") (Lin et al., *Cancer Res.* 37:44304438 (1977); Essigman et al., *Proc. Natl. Acad. Sci. USA* 74:1870-1874 (1977); Martin et al., *Nature* (London) 267:863-865 (1977)). The $AFB_1$-N-7-Gua adduct and its putative derivatives (2,3-dihydro-2-(N-5-formyl-2',5',6'-triamino-4'-oxo'N5-pyrimidyl)-3-hydroxy-aflatoxin $B_1$) ("AF-N7-Gua") have been identified in a wide variety of tissues and systems such as rat liver in vivo, cultured human bronchus and colon, and human lung cells in culture after acute or chronic administration (Haugen et al., *Proc. Natl. Acad. Sci. USA* 78:4124-4127 (1981)).

Some investigations regarding quantitation of aflatoxin $B_1$ and its metabolites including its DNA adduct have been conducted using immunological techniques and monoclonal antibodies (Hertzog et al., *Carcinogensis* 3:825-828 (1982); Groopman et al., *Cancer Res.* 42:3120-3124 (1982); Haugen et al., *Proc. Natl. Acad. Sci. USA* 78: 412-44127 (1981)). Similar research has been conducted utilizing immunological techniques and reagents for other low molecular weight toxins found in our environment (Johnson et al., *J. Analyt. Toxicol.* 4:86-90 (1980); Sizaret et al., *J.N.C.I.* 69:1375-1381 (1982); Hu et al., *J. Food Prot.* 47:126-127 (1984); and Chu, *J. Food Prot.* 47:562-569 (1984)).

U.S. Pat. No. 4,818,687 describes a general non-invasive screening procedure for assessing the exposure of humans and animals to environmentally occurring carcinogens. Therein, an affinity matrix and a method for the detection of low molecular weight compositions such as aflatoxins are provided utilizing specific monoclonal IgM antibody.

Affinity columns for detecting the presence of a single analyte, for example, one of aflatoxin, ochratoxin, zearalenone, deoxynivalenol or fumonisin, in a sample are well known. An affinity column for detecting both aflatoxin and ochratoxin in a single sample as well as an affinity column for detecting aflatoxin, ochratoxin and zearalenone have been commercially available. However, columns targeting higher numbers of chemical species necessarily must capture more diverse analytes. Aflatoxin is a large aromatic, multi-ring structure. Deoxynivalenol (DON) is a highly polar toxin that is smaller than a molecule of table sugar-sucrose. The lipid-like fumonisin shares structural characteristics with sphingolipids. Thus, the preparation of multi-analyte columns and their methods of use increase in complexity far out of proportion to the number of toxins being added for analysis. Column development must allow for treatment of all target analytes according to similar methods, in order that they all be analyzed with a single column.

There have been numerous reported incidences of naturally-occurring mycotoxins such as, aflatoxin $B_1$, $B_2$, $G_1$, $G_2$ and $M_1$ (Afla), deoxynivalenol (DON), fumonisin $B_1$, $B_2$ and $B_3$, ochratoxin A (OTA), and zearalenone (Zear) in various substrates. Malt beverages and wines can contain different multi-toxin combinations from fungi-infected grains and fruits used in the production. A desire still exists for competent multi-analyte columns for analyzing a plurality of toxins with a single column.

SUMMARY OF THE INVENTION

It is not possible to obtain satisfactory analytical results in a multi-analyte column by merely combining the quantities of resin used in a single analyte column to analyze each particular analyte. The invention is based, at least in part, on the discovery that satisfactory analytical results are possible by incorporating into the column antibodies that are specific for the analytes to be analyzed.

Thus the present invention provides a multi-analyte column capable of analyzing a single sample containing one or more of aflatoxin, deoxynivalenol ("DON"), fumonisin, ochratoxin, T-2 (and/or HT-2) and zearalenone. The multi-analyte columns in accord with the present invention comprise a first quantity of a first resin comprising an antibody having specificity for aflatoxin, a second quantity of a second resin comprising an antibody having specificity for deoxynivalenol, a third quantity of a third resin comprising an antibody having specificity for fumonisin, a fourth quality of a fourth resin comprising an antibody having specificity for ochratoxin, a fifth quantity of a fifth resin comprising an antibody having specificity for T-2 (and/or HT-2) and a sixth quantity of a sixth resin comprising an antibody having specificity for zearalenone.

It is desirable to obtain at least a 60%, preferably at least a 70% recovery from the column for each toxin in the sample. It also is desirable to have a column flow rate of at least 3 ml per minute, preferably so that a 10 ml sample will flow through the column in less than 5 min.

In one embodiment of the invention, a multi-analyte column capable of analyzing a single sample containing aflatoxin, deoxynivalenol, fumonisin, ochratoxin, T-2 (and/or HT-2) and zearalenone, comprises for each unit of resin containing antibody having specificity for ochratoxin, about 0.95 to 1.05 units of resin containing antibody having specificity for zearalenone, about 1.9 to 2.1 units of resin containing antibody having specificity for aflatoxin, about 2.35 to 2.65 units of resin containing antibody having specificity for fumonisin, about 2.8 to 3.2 units of resin containing antibody having specificity for T-2 (and/or HT-2) and about 4.7 to 5.3 units of resin containing antibody having specificity for deoxynivalenol. As used herein, one unit of resin is defined as the quantity of resin containing antibody that will bind 50 ng of aflatoxin, 500 ng of deoxynivalenol, 3300 ng of fumonisin, 50 ng of ochratoxin, 830 ng of T-2 (and/or HT-2) or 1140 ng of zearalenone, respectively. Such resin typically will contain about 5 mg antibody per ml of resin. However, any suitable loading of antibody on the resin can be used in accord with quantities and methods well known to those skilled in the art.

In a preferred embodiment, the multi-analyte column of the present invention is capable of analyzing a sample to detect aflatoxins $G_1$, $G_2$, $B_1$, $B_2$ and $M_1$, DON, fumonisins $B_1$, $B_2$ and $B_3$, ochratoxin A, T-2 and HT-2, and zearalenone in the analysis of a single sample applied to the column.

The invention also provides a method for analyzing a single sample for aflatoxin, deoxynivalenol, fumonisin, ochratoxin, T-2 (and/or HT-2) and zearalenone, the method comprising providing a multi-analyte column as described herein, applying liquid sample suspected of containing one or more of the specified toxins to bind any of the specified toxins to resins in the column, washing the column, eluting the resins and analyzing the eluant for the presence of each of the specified toxins. The liquid sample can be a liquid suspected of containing toxins or a liquid extract of a solid material suspected of containing toxins. Specific examples of sample materials that can be analyzed in accord with the columns of the present invention include fungi-infected grains and fruits, and alcoholic beverages such as, for example, malt beverages and wines.

DETAILED DESCRIPTION OF THE INVENTION INCLUDING PREFERRED EMBODIMENTS

In accord with the present invention, a multi-analyte column capable of analyzing a single sample containing aflatoxin, deoxynivalenol, fumonisin, ochratoxin, T-2 (and/or HT-2) and zearalenone can be prepared. Resins containing antibody having specificity for each of the toxins are included. Antibodies are raised by well known techniques and monoclonal antibodies are prepared having specificity for each toxin. Resins having each antibody bound thereto are prepared by techniques well known to those skilled in the art. Any resin material known by those skilled in the art to be useful for carrying attached antibodies can be used. A preferred resin material is Sepahrose® 4B available from Amersham Biosciences (Piscataway, N.J.). The antibodies are then attached to the resin using techniques well known to those skilled in the art. Preferably, about 5 mg of antibody is bound to one ml of resin. The resin preferably has a particle size range of about 45 to about 165 μm.

Columns are then prepared using appropriate quantities of each resin. For example, in one embodiment of the invention, in a 3 ml column having a diameter of 8.93 mm, a supporting porous disk, or the like, is positioned to support the resin bed while permitting flow out of the column. 200 μl of a first resin having an antibody specific for aflatoxin is layered on the disk. Then, 100 μl of a second resin having an antibody specific for ochratoxin is layered on the first resin. Then, 250 μl of a third resin having an antibody specific for fumonisin is layered on the second resin. Then, 100 μl of a fourth resin having an antibody specific for zearalenone is layered on the third resin. Then, 300 μl of a fifth resin having an antibody specific for T-2 (and/or HT-2) is layered on the fourth resin. 500 μl of a sixth resin having an antibody specific for DON is layered on the fifth resin. Finally, another porous disk, or the like, if desired, can be positioned to distribute the liquid sample across the column and/or hold the resin in place. Alternatively, the resins can be layered in any order or they can be mixed together and then loaded into the column as a mixture. Further, a suitable porous media such as, e.g., glass wool or the like, can be used in place of the porous disk.

For comparable size single analyte columns performing the same task, the same antibody/resins typically are loaded presently at 200-250 μl for aflatoxin, 200-250 μl for ochratoxin, 300 μl for T-2, 350 μl for fumonisin, 350 μl for zearalenone and 550 μl for DON.

In the above embodiment, 100 μl of resin is equal to one unit. Each unit of resin is capable of binding about 50 ng of aflatoxin, 500 ng of deoxynivalenol, 3300 ng of fumonisin, 50 ng of ochratoxin, 830 ng for T-2 (and/or HT-2) or 1140 ng of zearalenone, respectively. In accord with the invention, for each unit of resin having ochratoxin specific affinity, the column contains about 0.95 to 1.05 units of resin containing antibody having specificity for zearalenone, about 1.9 to 2.1 units of resin containing antibody having specificity for aflatoxin, about 2.35 to 2.65 units of resin containing antibody having specificity for fumonisin, about 2.8 to 3.2 units of resin containing antibody having specificity for T-2 (and/or HT-2) and about 4.7 to 5.3 units of resin containing antibody having specificity for deoxynivalenol.

The total amount of resin in the column should permit a sample fluid to flow through the column at a preferred rate of about 1-2 drops per sec.

For solid foods, preferably toxins are extracted from the food using a water-based or water compatible solvent such as, for example, water:methanol, water:acetonitrile, ethanol, water:ethanol, salt solutions, buffer solutions, and the like, etc. Such solvents are well known to those skilled in the art. Typically, in such solvents the organic component is greater. Extracts can be diluted with water prior to chromatography.

After loading the sample on the column, the column typically is washed to remove any extraneous materials that may be held up on the column so that only bound materials, i.e., the toxins, remain. The column generally can be washed with the water compatible solvent but typically having a greater water presence.

The column is eluted with solvents as is well known to those skilled in the art. The eluants preferably are analyzed for the particular analytes using HPLC/MS techniques.

Multi-analyte columns in accord with the present invention can be used as a clean-up step in analysis of extracts from solid materials or of liquid products such as alcoholic beverages for aflatoxins, fumonisins, ochratoxin A, deoxynivalenol, T-2 (and/or HT-2) and zearalenone, in combination with HPLC and/or mass spectrometry detection. LC/MS and LC/MS-MS methods for detection can also be used. Methods for detecting the toxins are well known to those skilled in the art.

Dried distiller's grains can contain naturally occurring multiple mycotoxins. A single sample of an alcoholic beverage can be analyzed for aflatoxin, deoxynivalenol, fumonisin, ochratoxin, T-2 (and/or HT-2) and zearalenone using the six analyte column of the present invention.

The following example illustrates detection of aflatoxins $G_1$, $G_2$, $B_1$, $B_2$, DON, fumonisins $B_1$, $B_2$, $B_3$, ochratoxin A, T-2 and zearalenone using a column containing 200 µl of a first resin having an antibody specific for aflatoxin, 100 µl of a second resin having an antibody specific for ochratoxin, 250 µl of a third resin having an antibody specific for fumonisin, 100 µl of a fourth resin having an antibody specific for zearalenone, 300 µl of a fifth resin having an antibody specific for T-2 and/or HT-2, and 500 µl of a sixth resin having an antibody specific for DON, wherein each resin has approximately 5 mg/ml of antibody and toxin detection capability per unit described herein. Spiked samples are used to calculate recovery from the column.

Materials and Methods
Apparatus and Equipment

A Shimadzu 2010 LC is fitted with an autosampler and a dual Mass Selective and UV Detector. The Shimadzu 2010 is used in two operating modes, positive for Aflatoxin ($B_1$, $B_2$, $G_1$, $G_2$), Fumonisin ($B_1$, $B_2$, $B_3$), Zearalenone, DON (Vomitoxin), and T2 and then switched to the negative mode for Ochratoxin. (In the positive mode, the ions are positively charged; in the negative mode, the ions are negatively charged. Ochratoxin is more readily detected in the negative mode.) The instrument is capable of operating in APCI (Atmospheric Pressure Chemical Ionization) or ESI (Electro Spray Ionization). Only the APCI was used for mycotoxins. The mobile phase differs between the two modes, with ammonium acetate/triethylamine in the negative mode and ammonium acetate/formic acid in the positive mode. The LC column is a C18 5µ pore that is 5 cm in length and 2.1 mm in diameter.

Analytical Conditions

The individual analytes are scanned to obtain major ions, and then an ion is selected that is free from interference and shows a linear response to increasing concentrations. Generally, a five (5) point curve is set up. The standards are stored in two sets. One set is just Ochratoxin, while the other is the combination of the other five standards. The run time is; about ten (10) minutes for the positive mode mycotoxins and about five (5) minutes for Ochratoxin. The instrument is capable of achieving <1 ppb levels for the four aflatoxins and 100 ppb for the fumonisins.

Sample Preparation and SPE Column Clean-Up Protocols

The samples are extracted using a methanol-water extraction solution and the extract is cleaned up and then put through Vicam affinity chromatography columns. The columns are eluted and the eluent analyzed by liquid chromatography/mass spectrometry (LC-MS).

DEFINITIONS

As used in the specification and claims, the singular forms "a", "an" and "the" include plural references unless the context clearly dictates otherwise. For example, the term "a molecule" also includes a plurality of molecules.

As used herein, an "analyte" is the element of the sample to be detected or isolated. An analyte includes, but is not limited to, a toxin, a toxoid, a toxic substance, a poisonous substance, a poison, or a specific impurity of interest. An analyte may be of biological or non-biological origin. In some embodiments, the analyte specifically binds a binding reagent. In some embodiments, the presence or absence of the analyte may be used to detect, for example, contamination of a sample. Alternatively, the presence or absence of the analyte may be used to determine the physiological condition of an organism from which the sample was obtained. A wide range of other uses will occur to one of skill in the art.

As used herein, a "toxin" includes a toxoid, a toxic substance, a poisonous substance, or a poison of biological or non-biological origin. In some embodiments, a toxin causes damage or disease to a cell or an organism.

As used herein, "specificity" refers to the ability of an antibody to discriminate between antigenic determinants. It also refers to the precise determinants recognized by a particular receptor or antibody. It also refers to the ability of a receptor to discriminate between substrates, such as drugs. With respect to nucleic acids, it refers to identity or complementarity as a function of competition or recognition/binding, respectively. "Specificity" of recognition or binding may be affected by the conditions under which the recognition or binding takes place (e.g., pH, temperature, salt concentration, and other factors known in the art).

As used herein, a "ligand" is a molecule or molecular complex that can be bound by another molecule or molecular complex. The ligand may be, but is not limited to, a molecule or molecular complex bound by a receptor, or it may be a complementary fragment of nucleic acid.

As used herein, an "antibody" (Ab) is protein that binds specifically to a particular substance, known as an "antigen" (Ag) (described infra). An "antibody" is any immunoglobulin, including antibodies and fragments thereof, that binds a specific epitope. The term encompasses polyclonal, monoclonal, and chimeric antibodies (e.g., multispecific antibodies).

As used herein, an "antigen" (Ag) is any substance that reacts specifically with antibodies or T lymphocytes (T cells). An "antigen-binding site" is the part of an immunoglobulin molecule that specifically binds an antigen.

As used herein, "biological sample" includes samples of tissues, cells, blood, fluid, milk, or other materials obtained from a biological organism. It also includes a biological organism, cell, virus, or other replicative entity.

As used herein, "food" includes any substance or product intended for human or animal consumption, regardless of nutritional value. "Food" includes beverages, including milk and water. It also includes ingredients or substances used in the preparation of food (e.g., oil, fat, spices, flavorings, etc.). "Food" may be processed, partially processed, or unprocessed. It can include artificial and/or natural ingredients.

As used herein, "beverage" or "drink" includes any liquid or colloidal substance intended for human or animal consumption, regardless of nutritional value. "Beverages" include milk and other dairy drinks (e.g., flavored milk, cream, eggnog, milkshakes, frappes), water, coffee and coffee-based beverages, tea and tea-based beverages, other infusions (e.g., herbal tea/tisane, roasted grain or nut beverages), beer, wine, other alcoholic substances (e.g., whisky, vodka, gin, brandy, rum, schnapps, liqueurs), fruit and vegetable juices and ciders, sap, soft drinks regardless of degree of carbonation (e.g., mixed juice beverages, syrup and powdered drinks, sodas and colas, sports and energy drinks), non-dairy milks (e.g., soy milk, rice milk, coconut or almond milk), hot chocolate, and hot cocoa. "Beverages" may be processed, partially processed, or unprocessed. Wine and beer may be alcoholic beverages, may have reduced alcohol or may be non-alcoholic. Coffee and tea may be undecaffeinated (i.e., "regular") or partially or wholly decaffeinated. Tea may be non-oxidized, partially oxidized, or fully oxidized. "Beverages" can include artificial and/or natural ingredients. "Beverages" may be enriched with vitamins and minerals or may be flavored with spices, herbs, seasonings, juices, flowers, berries, or other flavorings or substances (e.g., toasted rice).

When not otherwise stated, "substantially" means "being largely, but not wholly, that which is specified."

EXAMPLES

Example 1

Method 1.0 Liquid Chromatography/Mass Spectrometry (LC-MS):
  1.1 Column: Restek Allure C18, 50×2.1 mm, 5 µm particles, and Restek Ultra Aqueous C18 column, 50×2.1 mm, 5 µm particles will Trident 2 cm Guard column.
  1.2 Mobile phases:
    Solution A=0.5 mM ammonium acetate in water, 0.1% formic acid—positive mode
      0.1 mM ammonium acetate in water, 0.01% triethylamine—negative mode.
    Solution B=Acetonitrile/Methanol 50/50, 0.1% formic acid—positive mode
      Acetonitrile/Methanol 50/50—negative mode
  1.3 Gradient: Positive:
    0-0.5 min isocratic*=95% A, 5% B
    0.5-1.5 min linear gradient to 70% A, 30% B
    1.5 min-2 min isocratic—70% A, 30% B
    2 min-8 min linear gradient to 40% A, 60% B
    8 min-9 min linear gradient to 10% B, 90% B
    9 min-10 min isocratic=90% B
    10 min-10.2 min immediate return to 95% A, 5% B
    1.5 min delay of next injection
    Negative:
    0-1 min linear isocratic gradient to 95% A, 5% B
    1-1.5 min linear gradient to 70% A, 30% B
    1.5-4 min isocratic=50% A, 50% B
    4-4.5 min linear=50% A, 50% B
    4.5 min immediate return to 95% A, 5% B
    1.5 min delay of next injection
  *During "isocratic" periods, the percentages are held constant; during "linear" periods, the percentages change linearly.
  1.4 Flow rate: 0.7 mL/min.
  1.5 Column temperature: 40° C.
  1.6 Detection: Ions are chosen by running each standard or group of standards in scan mode first. Then an ion is picked for each of the mycotoxins with the least amount of interference from any of the other compounds. That ion is used in selective ion monitoring mode for quantitation and would be instrument/detector specific. For example, the user may choose to monitor a "parent ion" having, e.g., an extra proton or a "daughter ion" resulting from fragmentation.
  1.7 Injection volume: 50 µL
  1.8 Retention times: Positive Mode
    DON=1.6 min
    Aflatoxin G1=3.2 min
    Aflatoxin G2=3.5 min
    Aflatoxin B2=3.7 min
    Aflatoxin B1=4.1 min
    Fumonisin B1=5.8 min
    T2=6.9 min**
    Fumonisin B3=7.0 min**
    Zearalenone=7.3 min
    Fumonosin B2=7.8 min
    Total Run Time—11.5 min
  **Note that the molecular weights of these analytes differ so that mass spectrometry (i.e., ions are monitored individually) so these measurements do not overlap when analyzed via mass spectrometry.
  1.9 Retention times: Negative Mode
    Ochratoxin=2.6 min
    Total Run Time=6.5 min
2.0 Sample Extraction:
  2.1 Place 25 g of ground sample into centrifuge jar (without additional salt).
  2.2 Add to jar 100 mL methanol:water (80:20).
  2.3 Cover jar and shake on shaker for 2 minutes.
  2.4 Centrifuge at 5000 rpm for 10 minutes.
  2.5 Remove cover and pour liquid onto a glass fiber filter paper.
  2.6 Take filtered portion and place in 125 mL separatory funnel.
  2.7 Shake with 30-40 mLs hexane. Let separate.
  2.8 Discard hexane (top layer) and save aqueous portion.
  2.9 Repeat steps 2.6-2.8 again.
3.0 Sample Clean-up
  3.1 Pipet 10 mL filtered extract into a clean vessel.
  3.2 Dilute extract with 40 mL of PBS.
  3.3 Mix well. Filter through a glass fiber filter.
  3.4 Place in freezer for 1 to 2 hours.
  3.5 Filter through a glass fiber filter again.
4.0 Column Chromatography
  4.1 Remove two end caps from AOZFDT column.
  4.2 Attach column to outlet of reservoir on vacuum chamber.
  4.3 Pass 30 mL of diluted extract through the AOZFDT column at a steady slow flow rate of about 1-2 drops per second. Do not let column completely dry out. After 30 mLs is passed through column, gently pass a few seconds of air through column.
  4.4 After extract has passed through column, pass 10 mL PBS through the AOZFDT column at about 1-2 drops per second flow rate. Do not let column completely dry out. After 10 mL is passed through column gently pass a few second of air through column.
  4.5 Pass 10 mL water through the AOZFDT column. Gently pass a few seconds of air through the column.
  4.6 Elute AOZFDT column at flow rate of about 1 drop per second or less with 1.5 mL HPLC grade methanol and collect in a test tube. Gravity flow will generally provide a good flow rate, although other methods can be used.
  4.7 Transfer methanol into a 2 mL autosampler vial and cap for HPLC and/or mass spectrometry analysis.
  4.8 Run according to LC-MS instructions (above) for mass spectrometry analysis.

Example 2

Testing

The procedure described above was performed on ten (10) replicates of a sample of dried distiller's grains (DDG) with solubles spiked at the indicated levels. Ochratoxin was analyzed in the negative mode. All other toxins were analyzed in the positive mode.

Precisions and recoveries showed a good correlation with theoretical levels (parts per billion [ppb] or parts per million [ppm]) based on spiking. All recovery values were above 70%, with most above 90%. The average values and percentages of residual standard deviation (% RSD) are provided.

TABLE 1

Results.

| Mycotoxin | Sample | Theoretical Level | | % Recovery | Average | % RSD |
|---|---|---|---|---|---|---|
| Aflatoxin B1 | DDG | 10 | ppb | 99.5 | 9.95 | 0.63 |
| Aflatoxin B2 | DDG | 2.5 | ppb | 98.7 | 2.47 | 1.43 |
| Aflatoxin G1 | DDG | 10 | ppb | 100 | 10.0 | 0.58 |
| Aflatoxin G2 | DDG | 2.5 | ppb | 96.0 | 2.40 | 2.99 |
| Fumonisin B1 | DDG | 1 | ppm | 106 | 1.06 | 2.30 |
| Fumonisin B2 | DDG | 0.75 | ppm | 76.8 | 0.576 | 10.2 |
| Fumonisin B3 | DDG | 1 | ppm | 85.1 | 0.851 | 6.14 |
| Deoxynivalenol | DDG | 1 | ppm | 84.1 | 0.841 | 6.37 |
| T2 | DDG | 1 | ppm | 109 | 0.547 | 3.47 |
| Zearalenone | DDG | 500 | ppb | 76.4 | 381 | 10.3 |
| Ochratoxin | DDG | 10 | ppb | 103 | 10.3 | 3.62 |

Throughout this application, various publications including United States patents, are referenced by author and year and patents by number. The disclosures of these publications and patents in their entireties are hereby incorporated by reference into this application in order to describe more fully the state of the art to which this invention pertains.

The invention has been described in an illustrative manner, and it is to be understood that the terminology which has been used is intended to be in the nature of words or description, rather than of limitation.

Modifications and variations of the present invention are possible in light of the above teachings. It is, therefore, to be understood that within the scope of the described invention, the invention may be practiced otherwise than as specifically described.

The present inventions have been described in detail including preferred embodiments thereof. However, it should be appreciated that those skilled in the art, upon consideration of the present disclosure, may make modifications and improvements within the spirit and scope of the present inventions.

What is claimed is:

1. A multi-analyte column comprising at least one unit of resin having ochratoxin specific affinity and, for each unit of resin having ochratoxin specific affinity, the column further contains about 0.95 to 1.05 units of resin containing antibody having specificity for zearalenone, about 1.9 to 2.1 units of resin containing antibody having specificity for aflatoxin, about 2.35 to 2.65 units of resin containing antibody having specificity for fumonisin, about 2.8 to 3.2 units of resin containing antibody having specificity for T-2 and/or HT-2 and about 4.7 to 5.3 units of resin containing antibody having specificity for deoxynivalenol (DON), wherein one unit of resin is the quantity of resin containing antibody that will bind 50 ng of aflatoxin, 500 ng of deoxynivalenol, 3300 ng of fumonisin, 50 ng of ochratoxin, 830 ng of T-2 and/or HT-2, or 1140 ng of zearalenone, respectively.

2. The multi-analyte column of claim 1, wherein the column is structured and arranged to have a column flow rate of at least 3 ml per minute.

3. The multi-analyte column of claim 1, wherein the column is capable of analyzing a sample to detect each of aflatoxins $G_1$, $G_2$, $B_1$, $B_2$, DON, fumonisins $B_1$, $B_2$, $B_3$, ochratoxin A, T-2 or HT-2, and zearalenone.

4. The multi-analyte column of claim 1, wherein the column is capable of analyzing a sample to detect each of aflatoxins $G_1$, $G_2$, $B_1$, $B_2$ and $M_1$, DON, fumonisins $B_1$, $B_2$, $B_3$, ochratoxin A, T-2 or HT-2, and zearalenone.

5. The multi-analyte column of claim 1, wherein a flow rate of sample fluid through the column is 1-2 drops per second.

6. The multi-analyte column of claim 1, wherein the resin has a particle size of about 45 to about 165 μm.

7. The multi-analyte column of claim 1, wherein the resin comprises about 5 mg of antibody per ml of resin.

8. The multi-analyte column of claim 1, wherein one resin having a toxin specific affinity is layered into a column followed successively by layering into the column another resin having a different toxin specific affinity until all of the resin is in the column.

9. The multi-analyte column of claim 1, wherein the resins having different toxin specific affinity are mixed and placed into a column.

10. A method of analyzing a single liquid sample for aflatoxin, deoxynivalenol, fumonisin, ochratoxin T-2 and/or HT-2, and zearalenone, the method comprising:
   providing a multi-analyte column comprising at least one unit of resin having ochratoxin specific affinity and, for each unit of resin having ochratoxin specific affinity, the column further contains about 0.95 to 1.05 units of resin containing antibody having specificity for zearalenone, about 1.9 to 2.1 units of resin containing antibody having specificity for aflatoxin, about 2.35 to 2.65 units of resin containing antibody having specificity for fumonisin, about 2.8 to 3.2 units of resin containing antibody having specificity for T-2 and/or HT-2, and about 4.7 to 5.3 units of resin containing antibody having specificity for deoxynivalenol (DON), wherein one unit of resin is the quantity of resin containing antibody that will bind 50 ng of aflatoxin, 500 ng of deoxynivalenol, 3300 ng of fumonisin, 500 ng of ochratoxin, 830 ng of T-2 and/or HT-2, or 1140 ng of zearalenone, respectively;
   loading the column with a predetermined amount of a liquid sample suspected of containing one or more of the toxins selected from aflatoxin, deoxynivalenol, fumonisin, ochratoxin, T-2, HT-2 and zearalenone;
   binding the toxins to the antibodies on the column;
   subsequently, eluting each of the toxins in eluant; and
   analyzing the eluant for the presence of each toxin.

11. The method according to claim 10, wherein toxins are extracted from a food using a water-based or water compatible solvent.

12. The method according to claim 11, wherein the solvent is water:methanol, water:acetonitrile, ethanol, water:ethanol, a salt solution or a buffer solution.

13. The method according to claim 10, wherein the liquid sample comprises a food extract.

14. The method according to claim 10, wherein the liquid sample comprises a grain extract.

15. The method according to claim 10, wherein the liquid sample comprises an alcoholic beverage.

16. The method according to claim 10, wherein the liquid sample comprises an extract from a food product or a liquid component of a food product.

17. The method according to claim 10, wherein the liquid sample comprises an extract from a grain or fruit to be analyzed for a fungi-infection.

18. The method according to claim 10, wherein the liquid sample is a malt beverage or wine.

19. A kit comprising the multi-analyte column according to claim 1 and instructions for use.

* * * * *